United States Patent
Glammeier

(10) Patent No.: US 9,254,241 B1
(45) Date of Patent: *Feb. 9, 2016

(54) HOLDING APPARATUS SYSTEMS FOR INJECTABLE FLUID BOTTLES

(71) Applicant: Lance Glammeier, Sioux Falls, SD (US)

(72) Inventor: Lance Glammeier, Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/637,052

(22) Filed: Mar. 3, 2015

Related U.S. Application Data

(60) Continuation-in-part of application No. 13/041,549, filed on Mar. 7, 2011, now Pat. No. 8,967,572, which is a division of application No. 11/483,945, filed on Jul. 10, 2006, now abandoned.

(51) Int. Cl.
| | | |
|---|---|---|
| *A47G 1/00* | (2006.01) | |
| *A61J 1/16* | (2006.01) | |
| *F16M 13/02* | (2006.01) | |
| *B65D 23/00* | (2006.01) | |

(52) U.S. Cl.
CPC . *A61J 1/16* (2013.01); *B65D 23/00* (2013.01); *F16M 13/02* (2013.01)

(58) Field of Classification Search
USPC .......... 248/316.1, 316.7, 316.8, 309.1, 316.2, 248/228.1, 228.2, 230.1, 230.2, 318.4, 248/219.3, 231.31, 534, 538, 539, 103, 248/224.14, 217.4, 689; 211/49.1, 69.8, 211/69.9, 124
See application file for complete search history.

(56) References Cited

U.S. PATENT DOCUMENTS

| | | |
|---|---|---|
| 2,051,408 A | 8/1936 | Karst |
| 2,496,478 A | 2/1950 | Kinnebrew |
| 2,569,021 A | 9/1951 | Rozanski |
| 3,602,370 A | 8/1971 | Jerch |
| 3,778,537 A | 12/1973 | Miller |
| 3,946,877 A | 3/1976 | Galicia |
| 4,909,467 A | 3/1990 | Shan-Pao |
| 4,974,807 A | 12/1990 | Moineau |
| 5,080,240 A | 1/1992 | Williams |
| 5,116,003 A | 5/1992 | Gerhardt |
| 5,322,256 A | 6/1994 | Kanwischer |
| 5,360,190 A | 11/1994 | Walker |
| 6,231,018 B1 | 5/2001 | Barbieri |
| 6,386,497 B1 | 5/2002 | Guyomard |
| 6,685,147 B1 | 2/2004 | Ma |
| 6,902,089 B2 | 6/2005 | Carnevali |
| 2008/0099648 A1 | 5/2008 | Broady |

*Primary Examiner* — Steven Marsh
(74) *Attorney, Agent, or Firm* — Jeffrey A. Proehl; Woods, Fuller, Shultz & Smith, P.C.

(57) ABSTRACT

A holding apparatus system for releasably holding injectable fluid bottles, comprising a pair of elongate elements for releasably gripping a neck portion of a bottle, and a retaining structure for permitting the elongate elements to be moved between a closed position configured to grip the neck portion of the bottle and an open position configured to release the neck portion of the bottle from being gripped by the elongate elements. In other embodiments, the elongate elements each have a first end and a second end, and the first ends of the elongate elements being relatively closer together than the second ends of the elongate elements so that the elongate elements diverge toward the second ends. A method of dispensing an injectable substance from a bottle using a bottle holder apparatus is also disclosed.

18 Claims, 13 Drawing Sheets

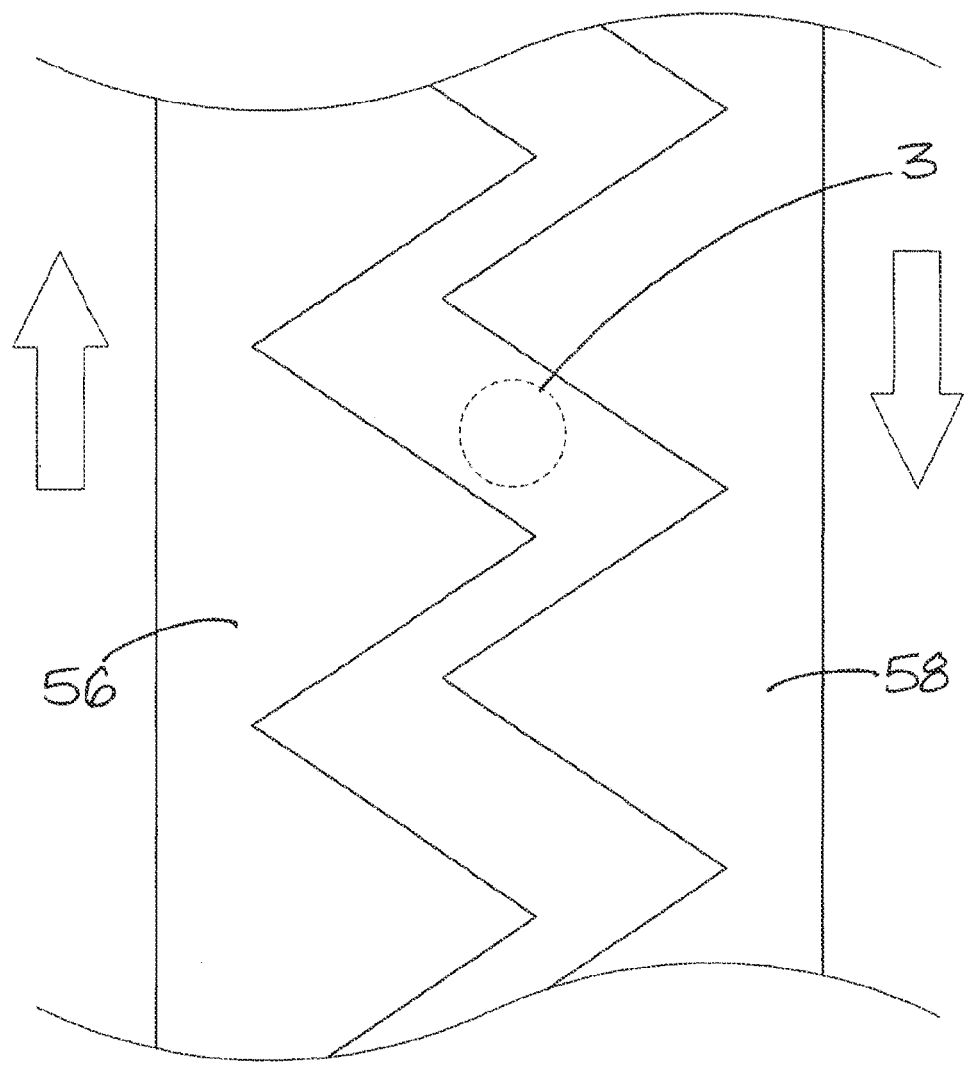

HOLDING APPARATUS SYSTEMS FOR INJECTABLE FLUID BOTTLES

REFERENCE TO RELATED APPLICATION

This application is a continuation-in-part application of my U.S. patent Ser. No. 13/041,549, filed Mar. 7, 2011, which was a divisional of my U.S. patent application Ser. No. 11/483,945 filed Jul. 10, 2006, abandoned, both of which are hereby incorporated herein in their entireties.

BACKGROUND OF THE INVENTION

1. Field of the Invention

The present invention relates to bottle holder and more particularly pertains to a new holding apparatus system for injectable fluid bottles for minimizing the exposure of health care workers and patients to unintended needle pricks, as well as helping keep the fluid bottles sterile and generally facilitating the control of health care costs.

2. Description of the Prior Art

Injecting substances, such as medications, using hypodermic needles and syringes is a common procedure in hospitals and clinics and doctor's offices, as well as in the homes of diabetics and other persons that depend upon daily injections. Additionally, injections are also commonly performed on farms. Typically, the injection requires the health care worker or doctor (or patient in the case of self-injections) to hold the bottle of medication in one hand, in an inverted position, and insert the needle into the bottle and partially withdraw the plunger of the syringe until a desired amount of the medication is withdrawn from the bottle. At that point, the tip portion of the needle is removed from the bottle and the bottle placed on a surface so that the injection can be administered.

However, each injection presents an opportunity for an accident, which can range from an unintended stick of the patient, the healthcare worker or a bystander, to an unintended squirting of the medication prior to the needle being inserted into the intended recipient of the medication. Quite often these accidents are the result of the practice of the person having to hold the needle in one hand and the bottle in the other hand, and then having to insert the sharp needle into the relatively small opening on the bottle (which is uniformly small regardless of the size of the body portion of the bottle). The insertion of the needle into the opening of the bottle thus presents a highly risky task, especially when it is repeated many times a day by a variety of staff persons.

Despite the inherent danger of this process, the procedure has remained basically the same for years. Even as concerns over the transmission of diseases through unintended needle pricks has led to improvements in the handling of discarded syringes and needles, the preparation and administration of injections has remained basically the same.

It is therefore felt that there is a significant need for improvements to the safety of this frequently repeated process, but an improvement that can benefit even those persons that self-inject only once a day.

SUMMARY OF THE INVENTION

In view of the foregoing disadvantages inherent in the known types of bottle holders now present in the prior art, the present invention provides a new holding apparatus system for injectable fluid bottles wherein the same can be utilized for minimizing the exposure of health care workers and patients to unintended needle pricks.

To attain this, the present invention generally comprises a holder apparatus for releasably holding injectable fluid bottles, which in one implementation comprises a pair of elongate elements for releasably gripping a neck portion of a bottle, and a retaining structure for permitting the elongate elements to be moved between a closed position configured to grip the neck portion of the bottle and an open position configured to release the neck portion of the bottle from being gripped by the elongate elements.

In another implementation of the invention, the holder apparatus for releasably holding injectable fluid bottles comprises a pair of elongate elements for releasably gripping a neck portion of a bottle. Each of the elongate elements have a first end and a second end, with the first ends of the elongate elements being relatively closer together than the second ends of the elongate elements so that the elongate elements diverge toward the second ends.

In another aspect of the invention, a method of dispensing an injectable substance from a bottle having a body portion and a constricted neck portion is disclosed, which includes providing a bottle holder comprising a pair of elongate elements for releasably gripping a neck portion of a bottle, with a portion of each of the elongate elements being positioned for gripping the neck portion of the bottle between the at least a portion of each of the elongate elements. The method may further include positioning the neck portion of the bottle between the portions of each of the elongate elements so that the neck portion is lodged between the portions of the elongate elements, and inserting a needle into an opening of the bottle as the neck portion of the bottle is lodged between the elongate elements.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

One significant advantage of the present invention is the capability to hold bottles of injectable substances away from the hands of the user, so that when a needle is inserted into the bottle, the hands are kept away from the needle and thus the chance of the user accidentally poking himself or herself with the needle while attempting to remove the fluid from the bottle and fill the syringe is minimized, if not virtually eliminated.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects of the invention will become apparent when consideration is given to the following detailed description thereof. Such description makes reference to the annexed drawings wherein:

FIG. 10 is a schematic top view of a portion of the pair of elongate elements having irregular, substantially "zig-zag" shaped opposing surfaces.

DESCRIPTION OF PREFERRED EMBODIMENTS

Figure 1:
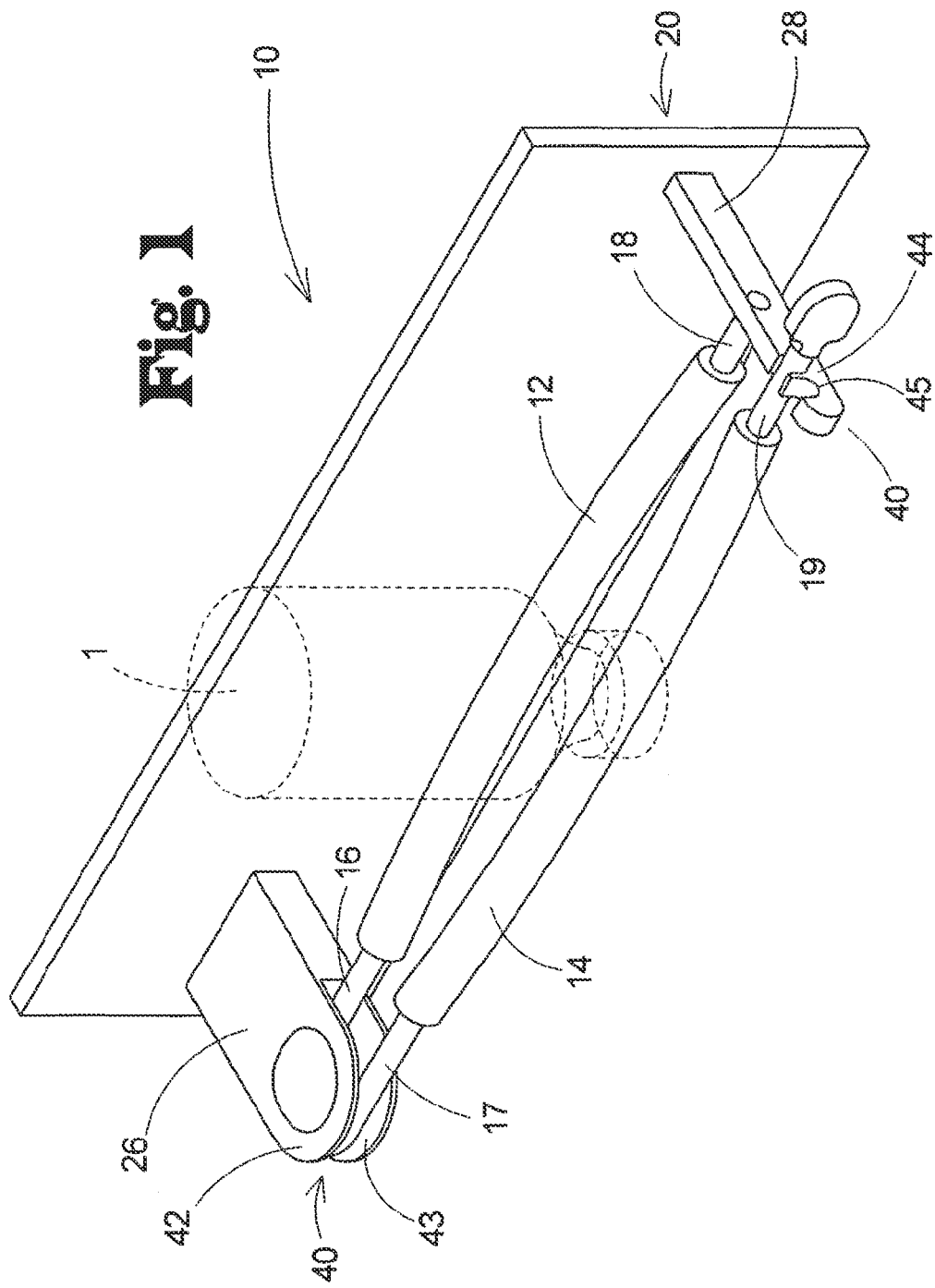
FIG. 1 is a schematic perspective view of a new holder apparatus for injectable fluid bottles according to the present invention.

With reference now to the drawings, and in particular to FIGS. 1 through 14 thereof, a new holding apparatus system for injectable fluid bottles embodying the principles and concepts of the present invention and generally designated by the reference numeral 10 will be described.

The holder apparatus 10 is highly suitable for holding injectable fluid bottles 1 in a manner that reduces the hand and skin of the user to the hypodermic needle as the needle is inserted through the mouth of the bottle and the fluid is drawn out of the bottle, as well as when the needle is withdrawn from the bottle. The bottle 1 of the injectable fluid typically has a body portion 2, a neck portion 3, and a mouth portion 4. The bottle also includes an interior 5 that holds the injectable fluid, and the interior at the neck portion 3 is typically relatively constricted in size with respect to the mouth 4 and body 2 portions. Although the size of the body portion 2 of the bottle 1 may vary in size according to the capacity of the bottle, the neck portion 3 is substantially uniform in size among bottles with different capacities (see FIG. 8). Typically, although not necessarily, the width or diameter of the neck portion if approximately ⅝ inches (approximately 1.6 cm). The mouth portion 4 includes an opening 6 into the interior of the bottle into which the needle is inserted, and the opening 6 may be covered by a membrane 7 that can be punctured by the needle. As the mouth portion 4 and opening 6 are typically relatively small to minimize the size of the membrane 7, the membrane "target" for the needle is relatively small and often difficult to engage and puncture, particularly if the person holding the syringe is distracted by conversation or other events occurring in the area of that person.

The holder apparatus 10 of the invention includes a structure for engaging the bottle in a secure yet easily manipulated manner. In embodiments of the invention, the holder 10 includes a pair of elongate elements 12, 14 that engage the bottle securely but permit relatively easy mounting of the bottle on the elements prior to use, and then removal of the bottle after the fluid has been drawn from the bottle. The elongate elements 12, 14 are positionable on opposite sides of the neck portion 3 of the bottle 1 in a manner that holds the neck portion in a substantially stationary condition (see FIG. 5), which permits the user to remove his or her hands from the bottle and thus permits the user to place both hands on the syringe if needed while the needle is inserted through the membrane 7 and into the interior 5 of the bottle and the syringe is manipulated to draw the fluid out of the interior and into the syringe.

In some embodiments of the invention, each of the elongate elements 12, 14 are substantially rigid to resist bending of the respective elongate element. Optionally, the each of the substantially rigid elongate elements may be slightly flexible to permit a small degree of bowing of the element, but elements 12, 14 having this character should exhibit sufficient resiliency so that if the element is bowed, the element will return to its shape (for example, linear) once the bowing force is removed. With these characteristics, the elements 12, 14 are highly suitable for pinching the neck portion 3 of the bottle 1 therebetween, especially when the separation distance between the normal positions of the elements 12, 14 is at least slightly less that the diameter of the outside surface of the neck portion 3 of the bottle. As a result, when the elements 12, 14 are positioned on either side of the neck portion 3, the elements abut against and apply a pinching force to the neck portion, and also resist movement of the mouth portion 4 (or the body portion 2) of the bottle 1 between and through the gap between the elements 12, 14. Each of the elements 12, 14 has a respective first end 16, 17 and a respective second end 18, 19.

In some embodiments of the invention, such as is shown in FIG. 1 through 6, the elongate elements 12, 14 are maintained in a substantially parallel relationship in which at least a portion of the length of the elements between the first and second ends thereof. The spacing of the inward facing surfaces of the uniformly spaced portions of the elements 12, 14 should be slightly less than the diameter of the outside surface of the neck portion of the bottle, which is typically approximately 0.5 to approximately 1.0 inches (approximately 1.2 to approximately 2.5 cm). It will be recognized that the more that the spacing distance is less than the neck portion diameter, the greater the hold on the bottle by the elements, but also the more difficult it may be for the user to place the neck portion between the elements and secure the elements, as will be further described below. Conversely, the closer the spacing distance between the elements 12, 14 is to the dimension of the neck portion, the more relatively loose the hold on the bottle will be, but the bottle may be easier to mount between the elements and secure the elements. As will be described in greater detail below, the positioning of the neck portion of a bottle between the elements 12, 14, may cause the surfaces of the elements to be somewhat deformed by the presence of the neck portion, such as is illustratively shown in FIG. 9c.

Figure 9A:
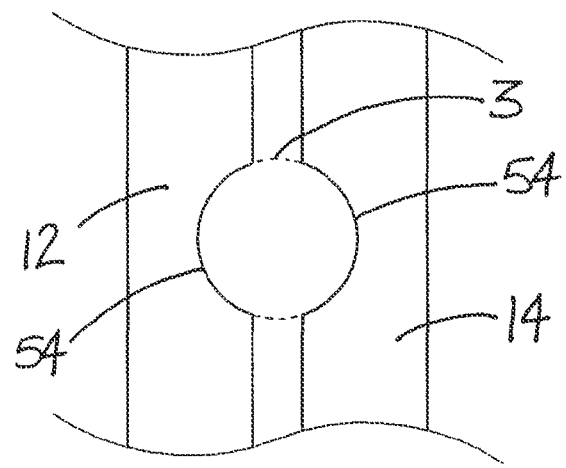
FIG. 9a is a schematic top view of a portion of the elongate elements showing an optional configuration in which each of the elements includes a notch for receiving a section of the neck portion of the bottle.
Figure 9B:
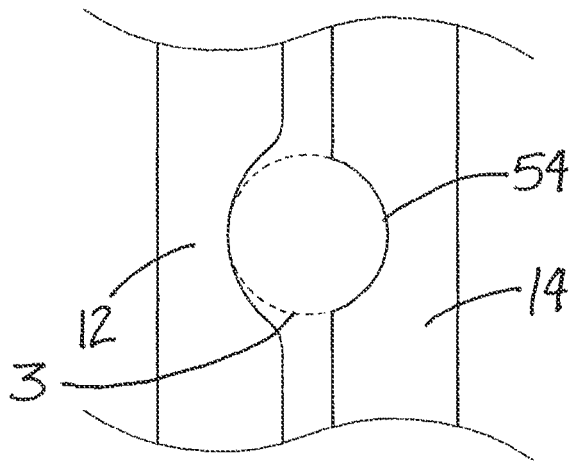
FIG. 9b is a schematic top view of a portion of the elongate elements showing an optional configuration in which one of the elements includes a notch for receiving a section of the neck portion of the bottle, and the other element does not.
Figure 9C:
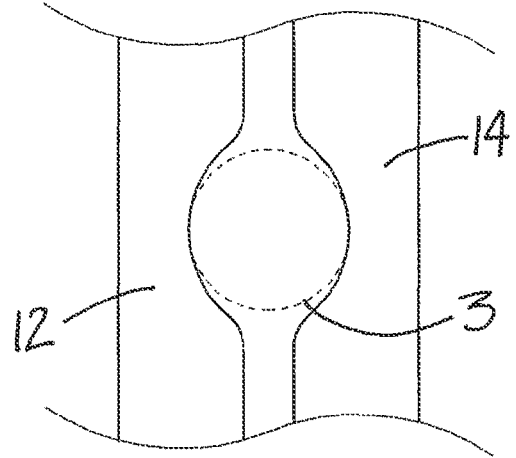
FIG. 9c is a schematic top view of a portion of the elongate elements showing an optional configuration in which neither of the elements includes a notch, and have surfaces that are substantially parallel to each other.

In other embodiments, such as shown in FIGS. 9a and 9b, one or both of the elongate elements 12, 14 may be shaped in some manner to accept the neck portion between the elements 12, 14. For example, as shown in FIG. 9a, each of the elements 12, 14 may be contoured with opposing notches 54 that each receive a section of the neck portion of the bottle positioned therebetween. This configuration of the elements 12, 14 can reduce the possibility of slipping of the neck portion along the gap between the elements, and may reduce the amount of pinching force that needs to be exerted by the elements on the bottle. As shown in FIG. 9b, only one of the elements 12, 14 may include a notch 54, while the opposing surface on the other element is relatively free of any notch, but still may be somewhat deformed by the presence of the neck portion of the bottle.

In yet another variation, as shown in FIG. 10, each of the elongate elements 56, 58, may have an irregular or "zig-zag" profile that generally fit with each other, and are longitudinally shiftable with respect to each other. In this embodiment, the gap between the opposed surfaces of the elements 56, 58 may be increased to permit the mouth portion of the bottle to be inserted through the gap between the opposing surfaces, and then the elements may be shifted in a reverse direction to grip the neck portions between the opposing surfaces.

It will be recognized that one, two, or more bottles may simultaneously be mounted on the elements 12, 14, which can facilitate situations where more than one injection of more than one fluid may be required, such as in the case of a surgical operation or an emergency room trauma unit.

Figure 7:
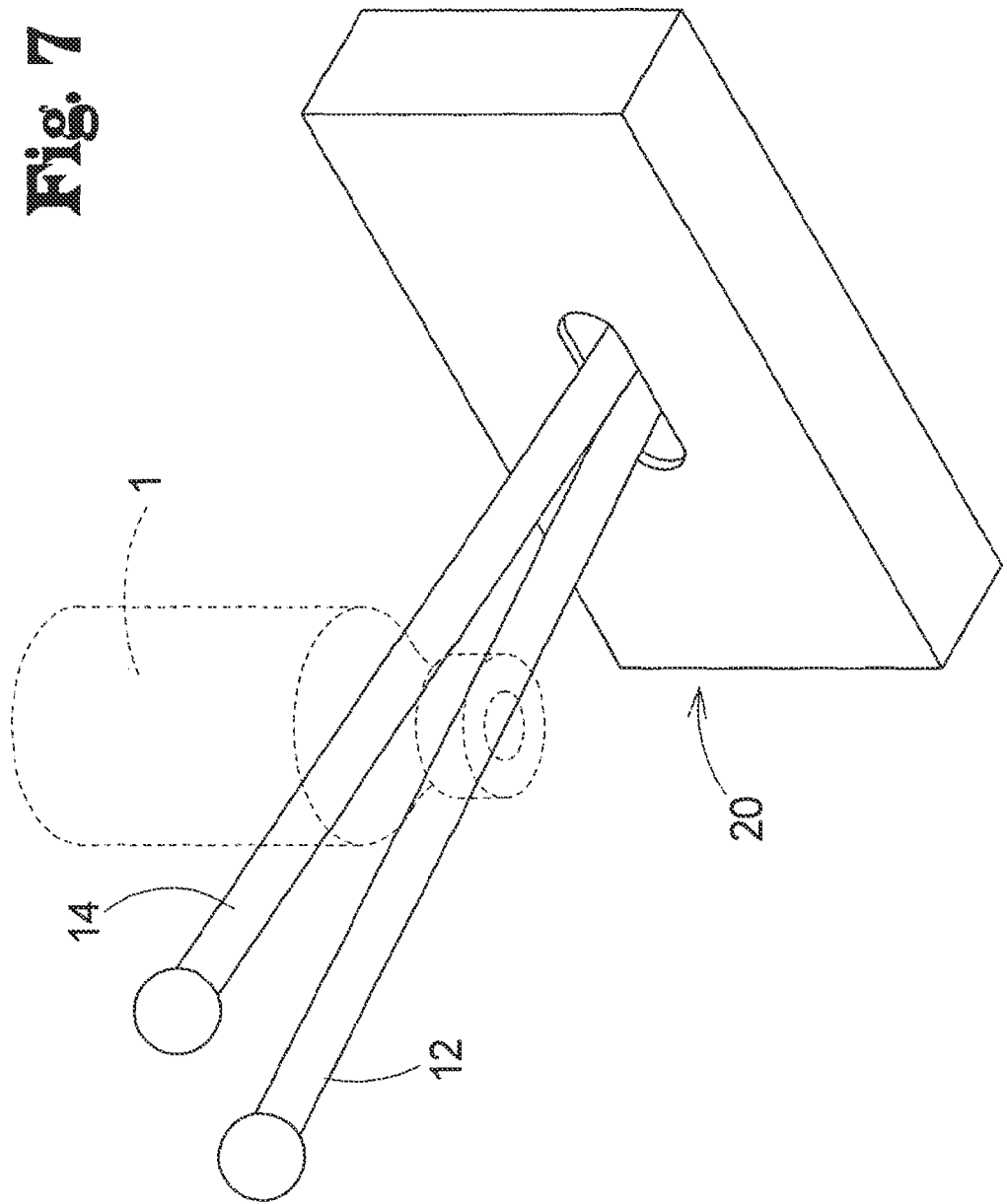
FIG. 7 is a schematic perspective view of another optional configuration of the present invention particularly illustrating the elongate elements in a substantially V-shaped arrangement.

In other embodiments of the invention, such as is shown in FIG. 7, the elongate elements 12, 14 are oriented with respect to each other in a divergent relationship, which may resemble a "V". In this orientation, the first ends 16, 17 of the elements 12, 14 are positioned relatively closer together than the second ends 18, 19 of the elements. The elements 12, 14 thus converge toward the first ends 16, 17 and diverge toward the second ends 18, 19. In these embodiments, the neck portion 3 of the bottle 1 is moved between the elements 12, 14 until the surfaces of both of the elements engage the neck portion, typically at opposite locations on the neck portion, and the neck portion may be effectively "wedged" between the elements. This effect may be created by some degree of resilient flexibility in the elements 12, 14. One advantage of this embodiment is the ability to accept and engage bottles having a wide range of diameters of neck portions, as the neck portion of the bottle is simply moved between the elements toward the converging first ends until the neck portion is felt to be sufficiently lodged between the elements so that the bottle will not be easily dislodged.

The bottle holder apparatus 10 of the invention may also comprise supporting structure 20 may also include structure for supporting the elongate elements 12, 14 on a vertical surface (e.g., a wall or a horizontal surface (e.g., a table or counter). The supporting structure 20 may include one or more standards 26, 28 that support the elongate elements 12, 14 on a support, such as, for example, a vertical surface or a horizontal surface. In some embodiments, a pair of the standards 26, 28 is employed and is positioned toward the ends 16, 17, 18, 19 of the elements 12, 14. In other embodiments, only one standard 26 may be employed.

The standard 26, 28 of the supporting structure 20 may include a base portion 30 for engaging a vertical or horizontal surface. The base portion 30 of the structure 20 may include means for mounting the base portion to the surface, such as one or more mounting apertures 32 that are located on the base portion that accept fasteners that are extended into a vertical or horizontal surface. The elongate elements 12, 14 may be mounted on the base portion 30, although in some embodiments the support structure 20 may also include an intermediate portion 36 that is mounted on the base portion 30 and the elements 12, 14 of the apparatus 10. In some embodiments, the intermediate portion 36 is pivotable with respect to the base portion 30 about an axis to permit pivot adjustment of the positioning of the elongate element 12, 14 with respect to the surface that the base portion engages. A pivot joint may join the base 30 and intermediate 36 portions together. In embodiments that employ only a single standard, an additional pivot joint may be employed to provide another axis of adjustment for the elongate elements 12, 14, relative to the surface.

In other embodiments, such as shown in FIG. 7, a supporting structure 36 is somewhat simpler in that the elongate elements 12, 14 merely need to be supported in a substantially immovable relationship (at least at the point of support for the elements).

The bottle holder apparatus 10 of the invention may further include retaining structure 40 for retaining at least a portion of the elongate elements 12, 14 in a suitable relationship to each other to permit a bottle (or multiple bottles) to be securely held between the elements, while also permitting the bottle or bottles to be readily mounted and dismounted. In some embodiments, such as those shown in FIGS. 1 through 6, the retaining structure 40 generally holds the first ends 16, 17 of the elongate elements 12, 14 in an adjacent (but typically spaced) relationship, and the retaining structure 40 releasably holds the second ends 18, 19 of the elongate elements in an adjacent (but typically spaced) relationship. The ends 16, 17, 18, 19 may be maintained at a spacing distance that is slightly smaller than the diameter of the neck portion, or the ends may be at different spacings than the portions of the elongate elements that are intended to engage the bottles.

In many embodiments, the retaining structure 40 permits the second ends 18, 19 of the elements 12, 14 to be moved away from each other to increase the space between the elements, at least toward the second ends. This capability to move the second ends apart permits the neck portions 3 of the bottles to be relatively easily inserted between the elements 12, 14 before the elements are moved back toward each other to apply a pinching force to the neck portions. In some embodiments, this movement occurs in both elongate elements 12, 14 (for example, both elements are movable), and in other embodiments the movement is substantially restricted to one 12 of the elongate elements, while the other element 14 is maintained in a substantially stationary condition. In either arrangement, the elongate elements 12, 14 are thus movable between a closed position (such as is shown in solid lines in FIG. 3) and an open position (such as is shown in broken lines in FIG. 3). In the closed position, the elongate elements 12, 14 may be positioned in a substantially uniformly spaced relationship capable of holding and constraining the neck portions of any bottles on the apparatus, while the presence of the neck portion between the elements may bow the elements outwardly somewhat from the substantially parallel relationship. In the open position, the elongate elements 12, 14 are moved out of the substantially uniformly spaced relationship, and may tend to diverge toward one end, to permit the loading or unloading of one or more bottles with respect to the apparatus 10. As previously noted, not all portions of the elongate elements 12, 14 need to be maintained in a uniformly spaced or parallel condition in the closed position, but it is believed that at least a portion of the elements should have a substantially uniformly spaced relationship to grip the neck portion of the bottle.

The retaining structure 40 may thus include means for holding the first ends 16, 17 together is a substantially rigid and immovable relationship to each other, so that the spacing between the first ends does not vary significantly as the elements 12, 14 are moved from the closed position to the open position. It should be noted at this point of the description that the elements 12, 14 are not necessarily two completely separate parts, but may be a single part or connected parts that are simply bent at the first ends 16, 17 of the elements to form the two elements. Thus, the single part could be a single part that is simply wrapped about a post and about which the elements 12, 14 are able to move to some degree. The first ends 16, 17 of the elements may be situated between plates 42, 43 that may or may not permit movement of the first ends with respect to each other. Those skilled in the art will recognize that many different structures may be constructed to establish the described relationship between the ends.

Figure 2:
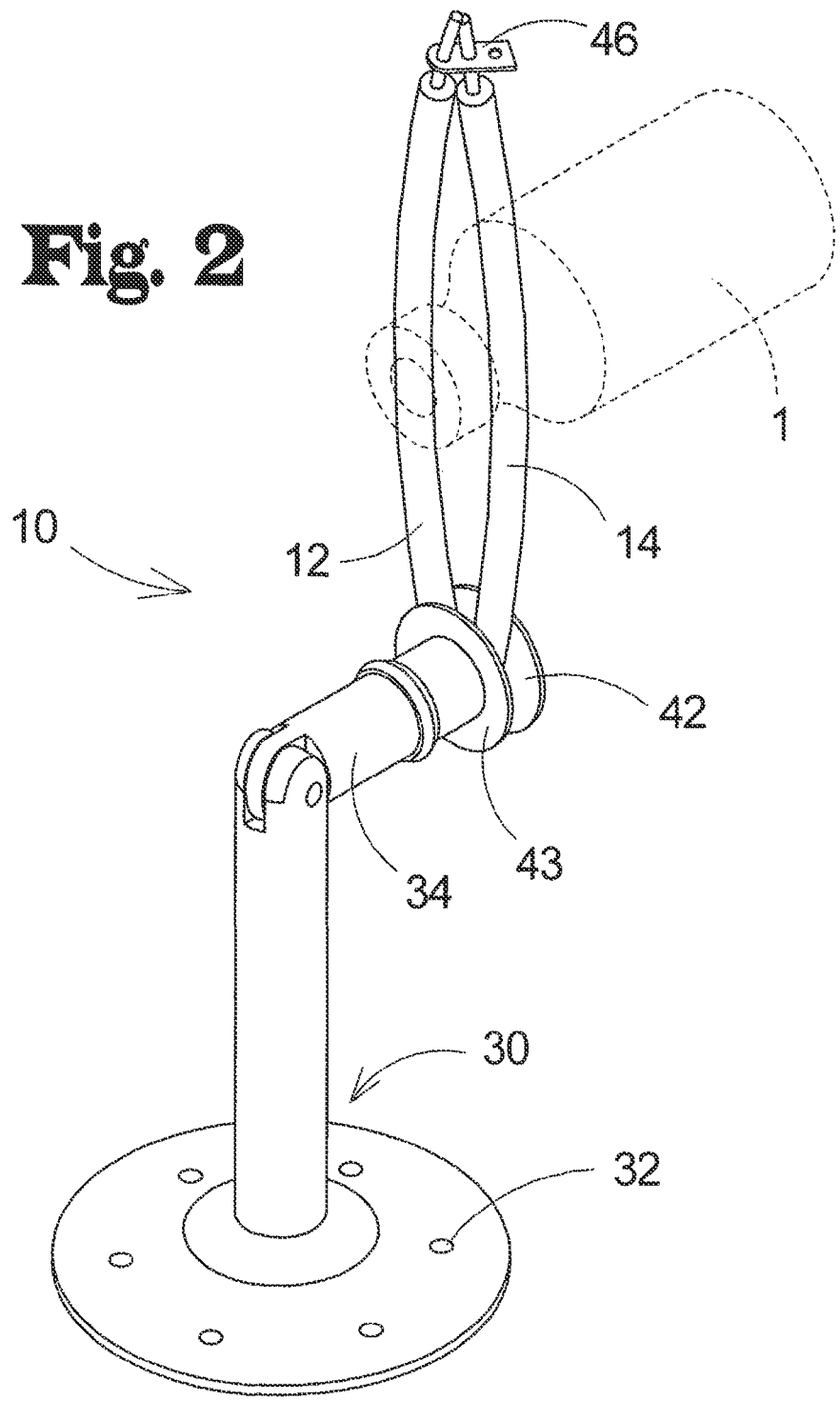
FIG. 2 is a schematic perspective view of an optional configuration of the present invention, particularly illustrating a supporting structure with a single standard.
Figure 3:
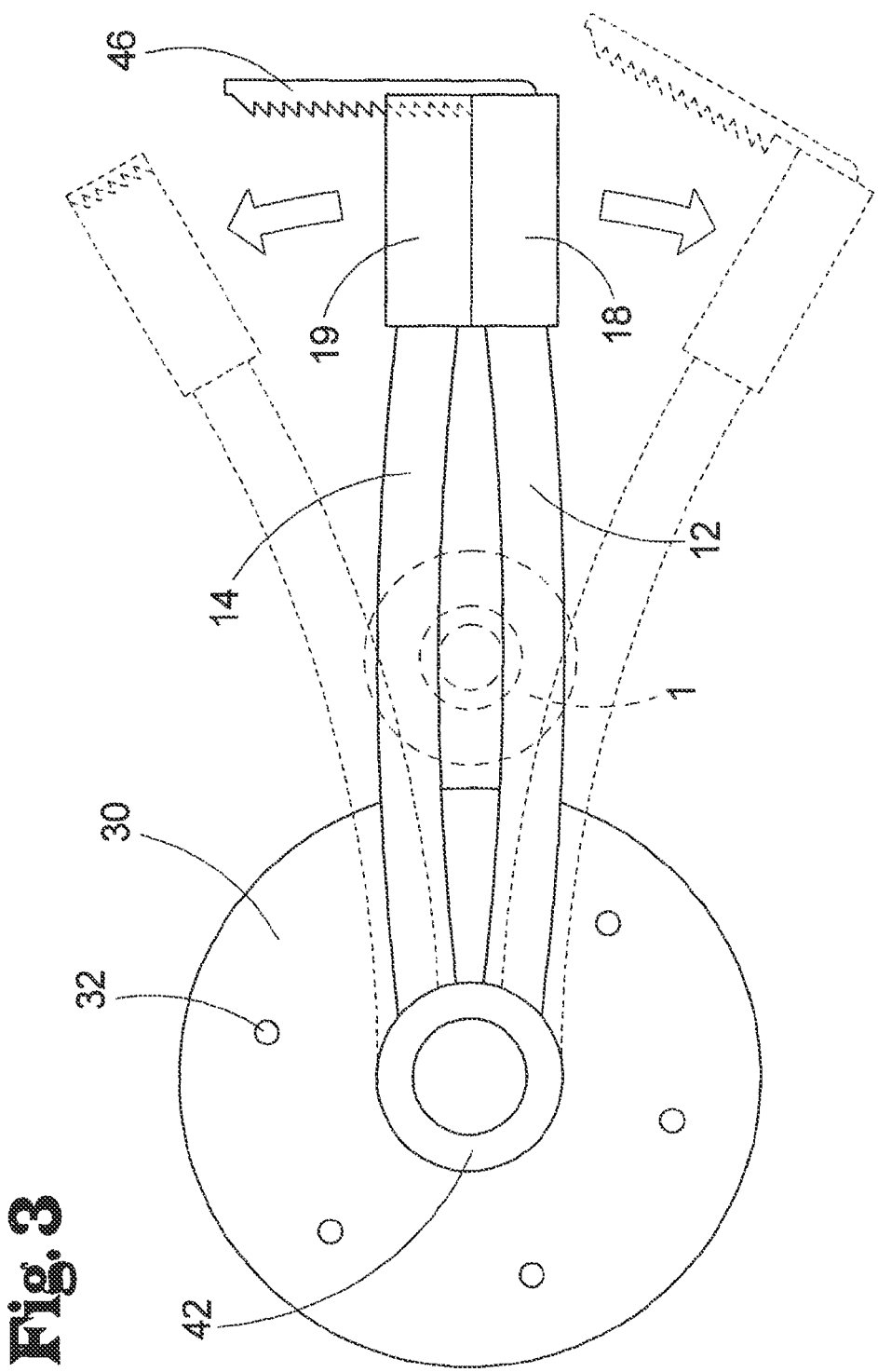
FIG. 3 is a schematic top view of the optional configuration of the present invention shown in FIG. 3.

In embodiments in which the elongate elements 12, 14 are moveable with respect to each other, the retaining structure 40 may also include means of holding the second ends 18, 19 of the elements 12, 14 in a substantially uniformly spaced relationship when the elements are in the closed position, as well as permitting the second ends to be selectively moved apart as the elements are moved from the closed portion to the open position. Again, those skilled in the art will recognize that there are a number of suitable structures for achieving this function, including structures for releasably connecting the second ends 18, 19 together. The drawings illustrate a number of optional structures for performing this function, but others may also be used. For example, as shown in FIG. 1, a bar 44 may be employed that is substantially permanently secured to the second end of one of the elements 12, 14 (preferably the second end of the relatively stationary element 12). The bar 44 may have at least one, and optionally more than one, slot 45 for removably receiving the second end of the movable element 14. Another example, as shown in FIGS. 2 and 3 of the drawings, a connecting structure may include an engaging arm 46 that is substantially permanently mounted on one of the elements and that releasably engages the other element.

Figure 4:
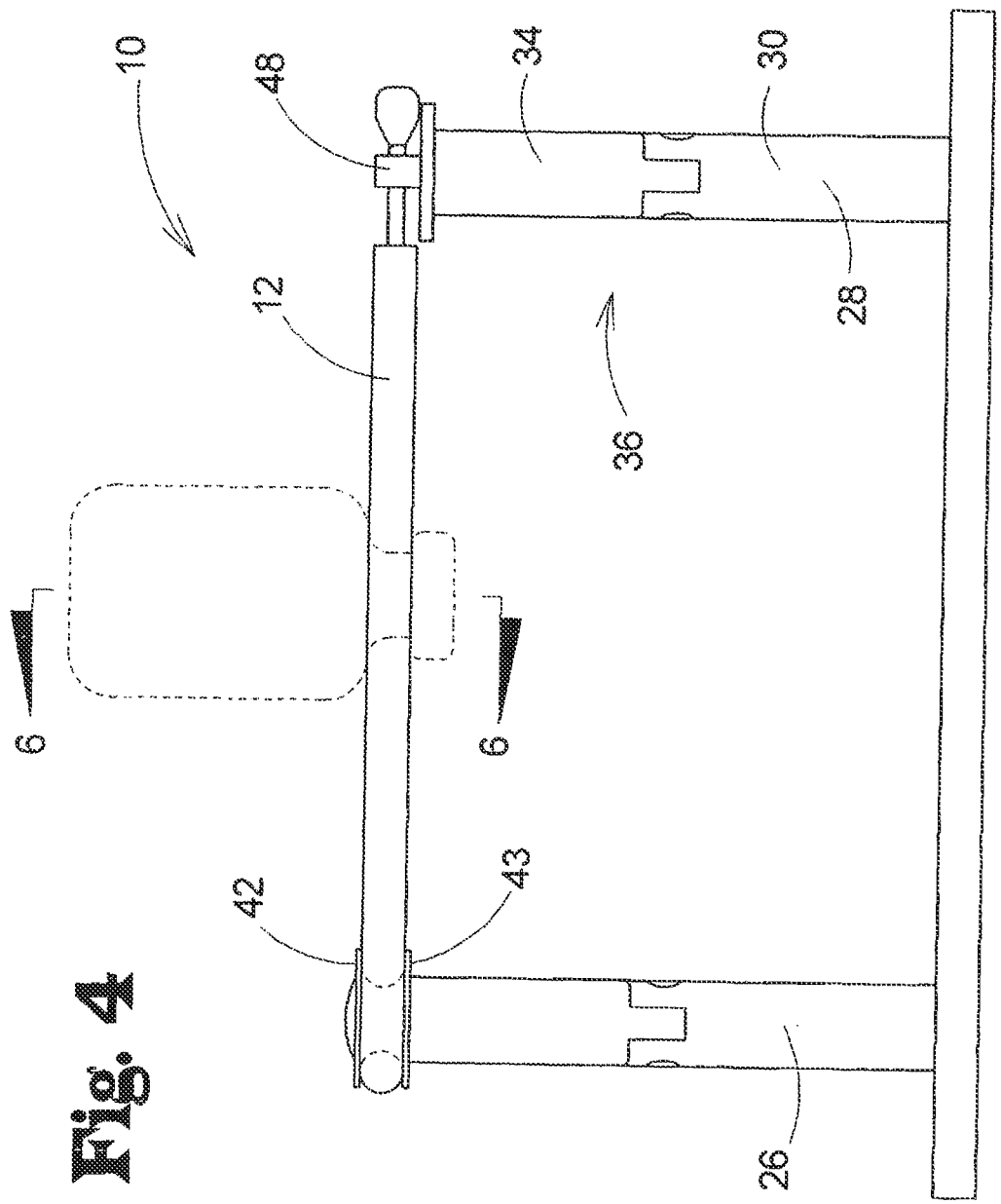
FIG. 4 is a schematic side view of another optional configuration of the present invention, particularly illustrating a supporting structure with two standards.
Figure 5:
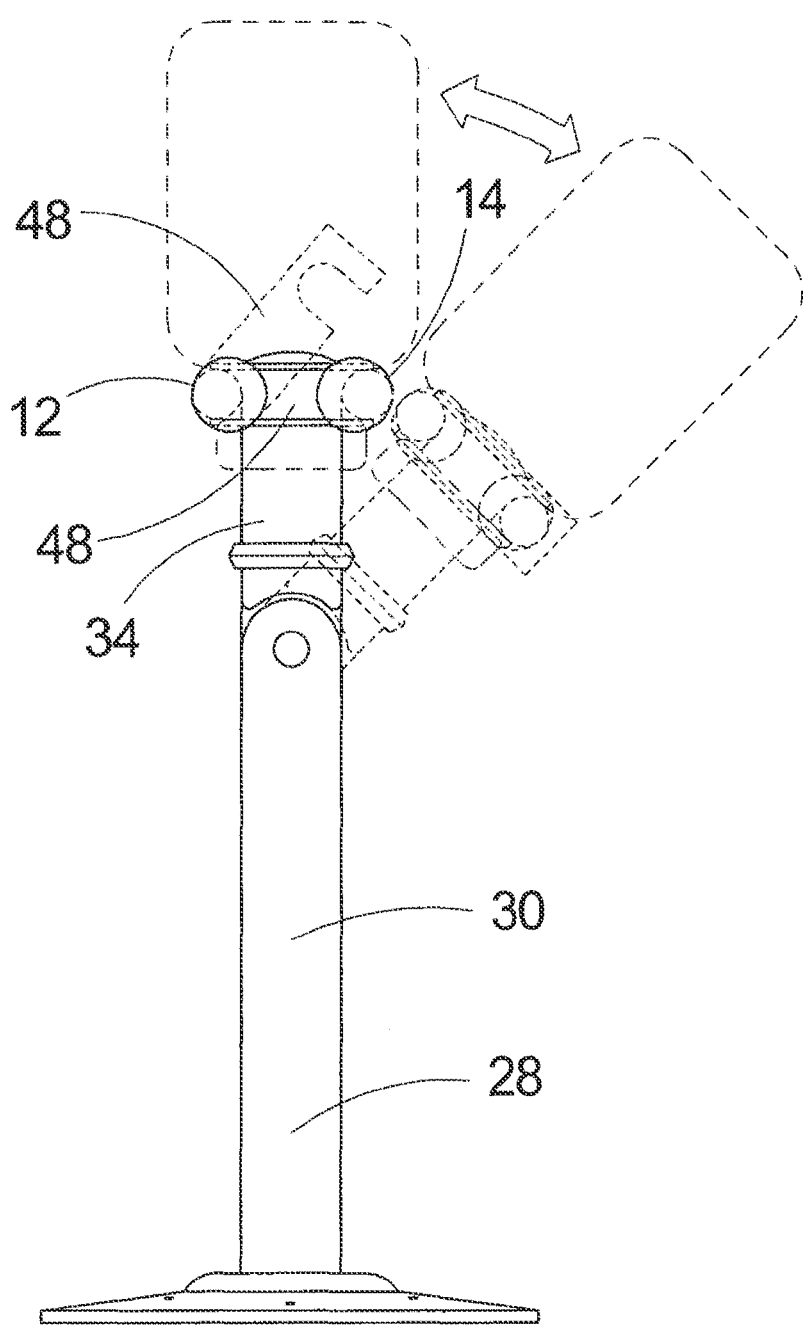
FIG. 5 is a schematic end view of the optional configuration of present invention shown in FIG. 4 showing the standards in an articulated condition.

Illustratively, the engaging arm 24 may include barbs or teeth that releasably engage substantially complementary teeth on the other elongate element to resist movement of the elements away from each other. In yet another example, such as is shown in FIGS. 4 and 5, a clip 48 is relatively permanently mounted on one of the elements 12, 14, and is able to releasably capture the other of the elements and hold the elements in the substantially uniformly spaced relationship. In some implementations, the clip 48 is rotatable (see FIG. 5) to assist in the capture and release of the movable element. These are only a few examples of various suitable structures that may be employed.

However, it is anticipated that embodiments in which the elongate elements 12, 14 are connected only at one end may be constructed, in which one of the elements pivots away from and toward the other element to load and unload bottles from the apparatus. In such embodiments, it is believed that there is a need to be able to securely lock the elements into a substantially uniformly spaced condition without the possibly that a bottle could be accidentally released from between the elements prior to intentional release of the bottle from between the elements. In other embodiments, there may be no connected between the elements 12, 14, which may be separately supported, and one or both of the elements may be laterally movable with respect to the other (see, for example, elements 60, 62 in FIG. 8).

In a significant aspect of the invention, at least one of the elongate elements, and in some embodiments, both of the elongate elements 12, 14, have a dual character. More specifically, at least one of the elongate elements 12, 14 has a compressible surface that exhibits a degree of resilient deformability for deforming when pressed against the surface of the neck portion of a bottle (see, for example, FIG. 9c), and then substantially recovers its shape after removed from contact with the bottle. To provide this character, at least one of the elements has an elastomeric coating that forms the surface of the element.

Figure 6:
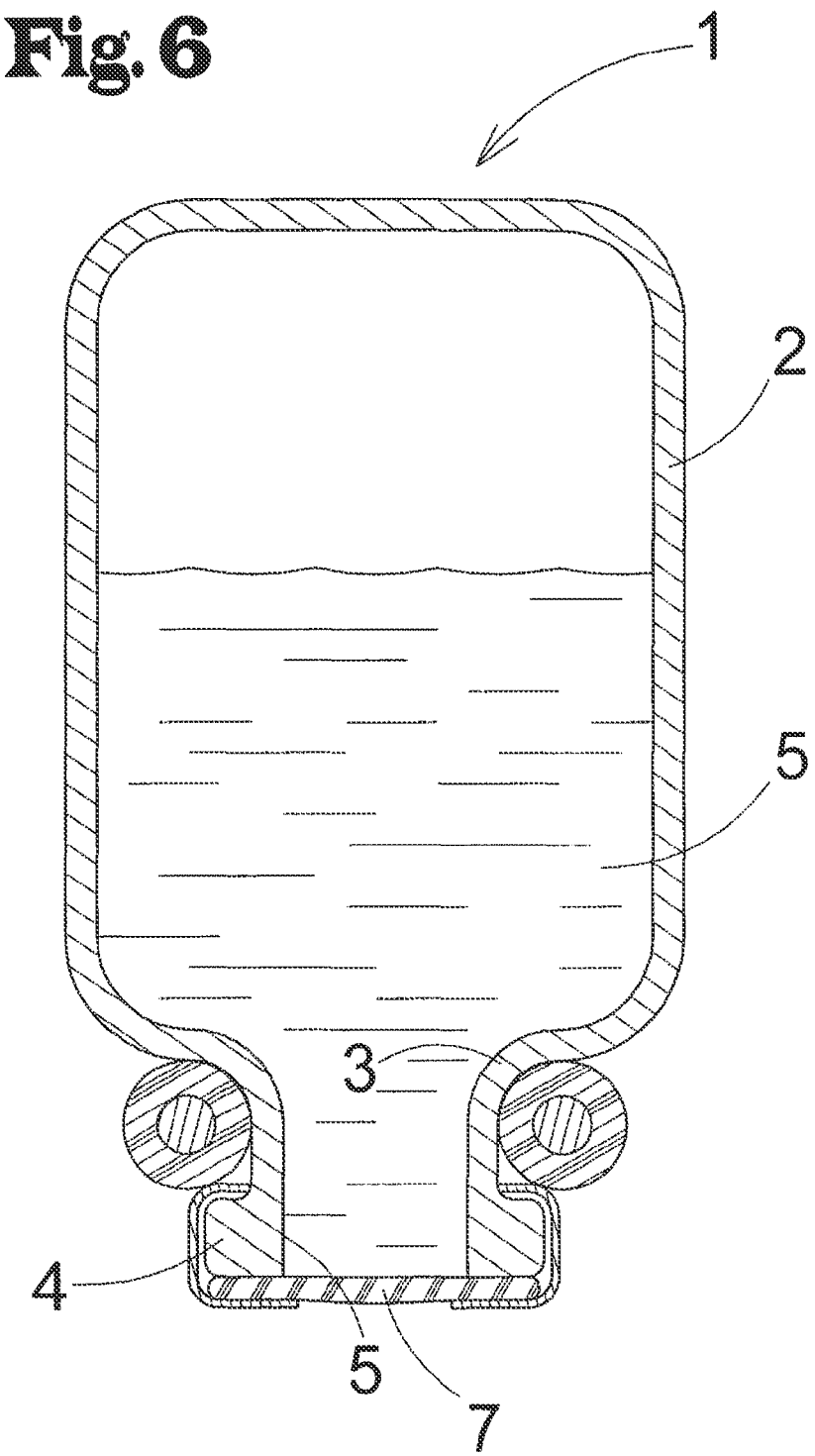
FIG. 6 is a schematic sectional view of the present invention taken along line 6-6 of FIG. 4.

Illustratively, as shown in FIG. 6, at least one of the elongate elements comprises a central rod 50 and an outer tube 52, with the central rod 50 being positioned in the outer tube 52. In some embodiments, the central rod comprises a substantially rigid material resistant to bending, and the outer tube comprises a compressible material. The central rod 50 thus provides the highly rigid character of the elements 12, 14, and the outer tube 52 is compliant or compressible to provide a "gripping" of the neck portion 3 of the bottle 1 that resists slippage or sliding of the bottle between the elements. In some embodiments, the central rod 50 may be formed of a metal that provides significant but not absolute resistance to bending, and the outer tube may comprise tubing formed of an elastomeric or rubber-like material.

Figure 8:
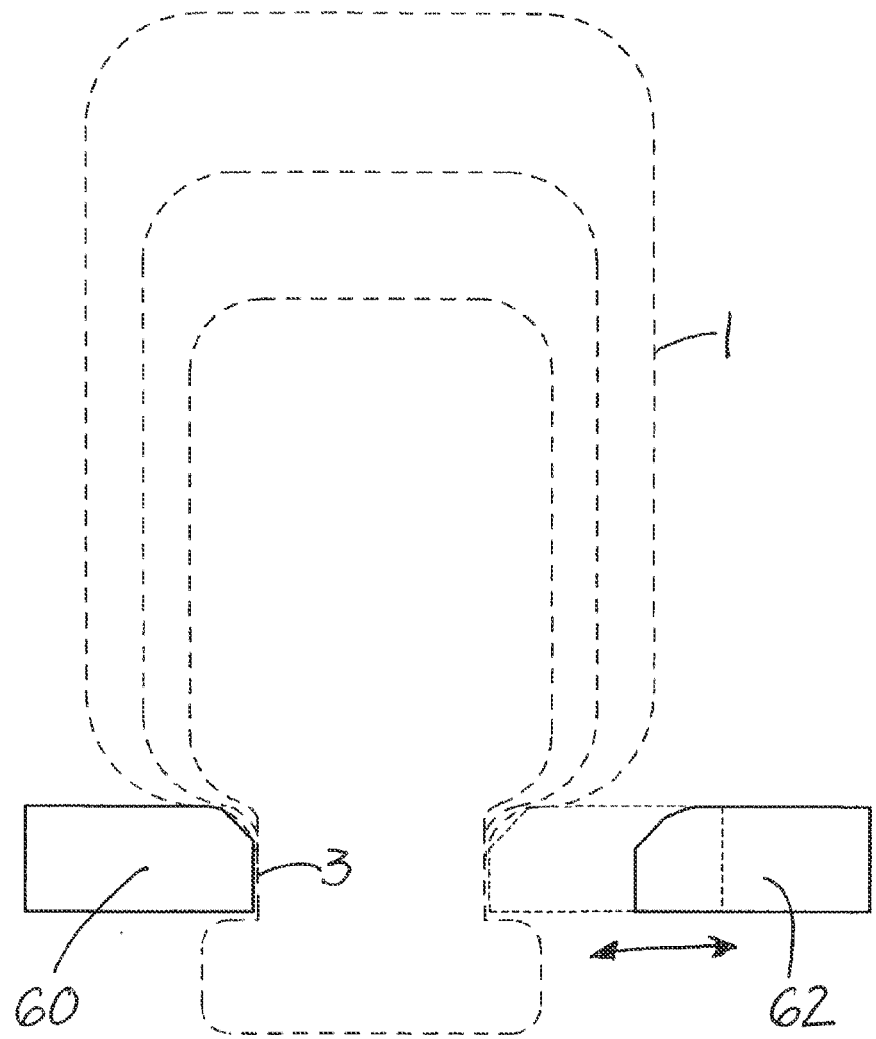
FIG. 8 is a schematic end view of the elongate elements showing one possible variation of the cross sectional shape of the elements, and illustrating lateral movement of the element or elements with respect to each other.

While some embodiments of the elongate elements 12, 14 have a substantially circular cross sectional shape, other cross sectional shapes may be employed. For example, shapes with relatively squared-off edges, as well as shapes that taper in thickness, may be employed. Illustratively, as shown in FIG. 8, elongate elements 60, 62 have edges and have a thickness that tapers thinner toward the contact surface area of the element.

In another aspect of the invention, a method of dispensing an injectable substance from a bottle is contemplated, and may use the bottle holder apparatus 10 of the invention. In one implementation of the method, the holder apparatus 10 is provided. The neck portion 3 of the bottle 1 is positioned between the elongate elements 12, 14. This step may be accomplished by moving one end of one of the elements 12, 14 away from the corresponding end of the other elongate element to thereby increase the distance between the elements, at least at one end of the elements. The movement of the ends apart may necessitate the release of a securing structure that holds the corresponding ends of the elements in the adjacent relationship. For example, the engaging arm 24 on one element may be released from engagement with the other element. In other embodiments of the invention in which the elements 12, 14 are substantially rigidly held in a V-shaped relationship (such as is shown in FIG. 7), there is no need to move the elements prior to insertion of the bottle therebetween.

Once the elements have been moved into an open position, the neck portion 3 of the bottle 1 may be positioned between the elongate elements 12, 14. One hand of the user may be used to maintain the movable element in a proximity to the stationary element such that the moveable element is able to be in contact with the neck portion of the bottle as it is moved between the elements (although the movable element is not held close enough to the stationary element to exert sufficient pinching force on the neck portion to prevent movement of the neck portion between the elements). The bottle 1 may be positioned at a medial location between the ends 16, 17, 18, and 19, or may be biased toward one end or the other. It should be recognized that more than one bottle may be situated between the elements 12, 14 at this time, and this may be accomplished by maintaining sufficient pressure by the hand of the user on the movable element to hold it against the first bottle while a second or subsequent bottle is slid between the elements. The larger size of the body portion 2 of the bottle relative to the neck portion resists slippage of the bottle between the elements while additional bottles are inserted.

In the case of the embodiment with the elements 12, 14 in the V-shaped configuration (FIG. 6), the neck portion may be slid between the elongate elements toward a position where the elongate elements converge toward each other, to a position where the neck portion is sufficiently lodged between the elements to resist movement of the bottle out of the lodged condition.

Once the bottle or bottles to be supported are positioned between the elements 12, 14, then the elongate elements may be moved toward each other with the neck portions of the bottle positioned therebetween. The elongate elements 12, 14 are pressed against the neck portion 3 of the bottle, which functions to pinch the neck portion between the elongate elements. The elements 12, 14 may be bowed or deformed outwardly from each other by the presence of the neck portions that are wider than the substantially uniform spacing of the elements. The resiliency of the elements 12, 14 tends to hold or grip the neck portions in a substantially stationary condition.

Once the bottle or bottles have been secured between the elements, the user may adjust the position or orientation of the bottle so that opening 6 of the mouth portion 4 is easily accessed, and so that the bottle (if not already) is positioned in an inverted orientation suitable for drawing fluid from the bottle. A needle is then inserted into the opening 6 of the bottle, and the substance or fluid is drawn from the bottle into the needle and the syringe. The needle and syringe may be used to inject the person.

The bottle or bottles may be removed from the holder apparatus 10 by essentially reversing the process used to mount the bottles, including releasing the pinching pressure of the elongate elements on the neck portion of the bottle by releasing the movable element and moving the elongate element away from the stationary element.

Figure 11:
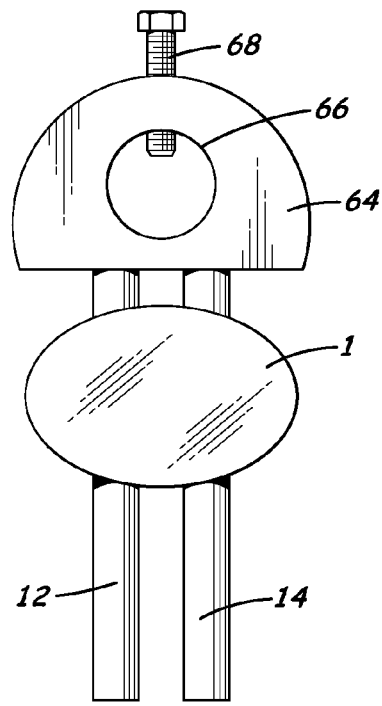
FIG. 11 is a schematic top view of a variation of the present invention which is highly suitable for mounting on an upright bar.

Another variation of the invention is shown in FIG. 11, which illustrates the apparatus with the elongate elements 12, 14 maintained in a substantially parallel and substantially fixed relationship by a base 64 on which the elements 12, 14 are mounted. The base 64 may include a hole 66 that may receive a bar or post or other upright for mounting the base on the upright for use. A fastener 68, such as a bolt, may be employed to selectively bear against an upright positioned in the hole 66 to secure the base 64 in position on the upright. This variation may be useful for mounting on medical apparatus support poles used, for example, by patients beds, or even on wheelchairs.

Figure 12:
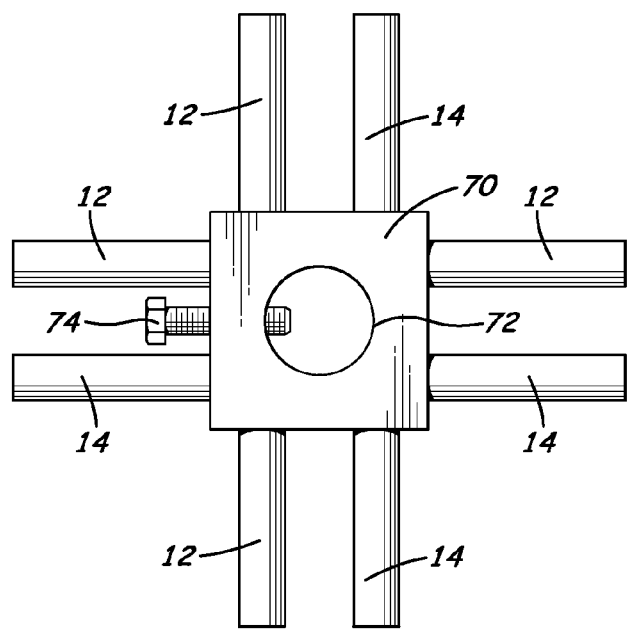
FIG. 12 is a schematic top view of a variation of the present invention which is highly suitable for mounting on an upright bar, and which includes a plurality of pair of elongate elements extending in different directions.

In another variation shown in FIG. 12, the apparatus includes a plurality of sets of elongates elements 12, 14 that are oriented in different directions from each other. For example, pair of the elements 12, 14 may be oriented in opposite directions, or may be oriented in directions that are orthogonal to each other, or in two, three, four or more different directions. In the illustrative embodiment, the pairs of elements 12, 14 extend in four different directions from the base 70, which may include a hole 72 and fastener 74 for securing the base 70 and elements 12, 14 in place on an upright.

Figure 13:
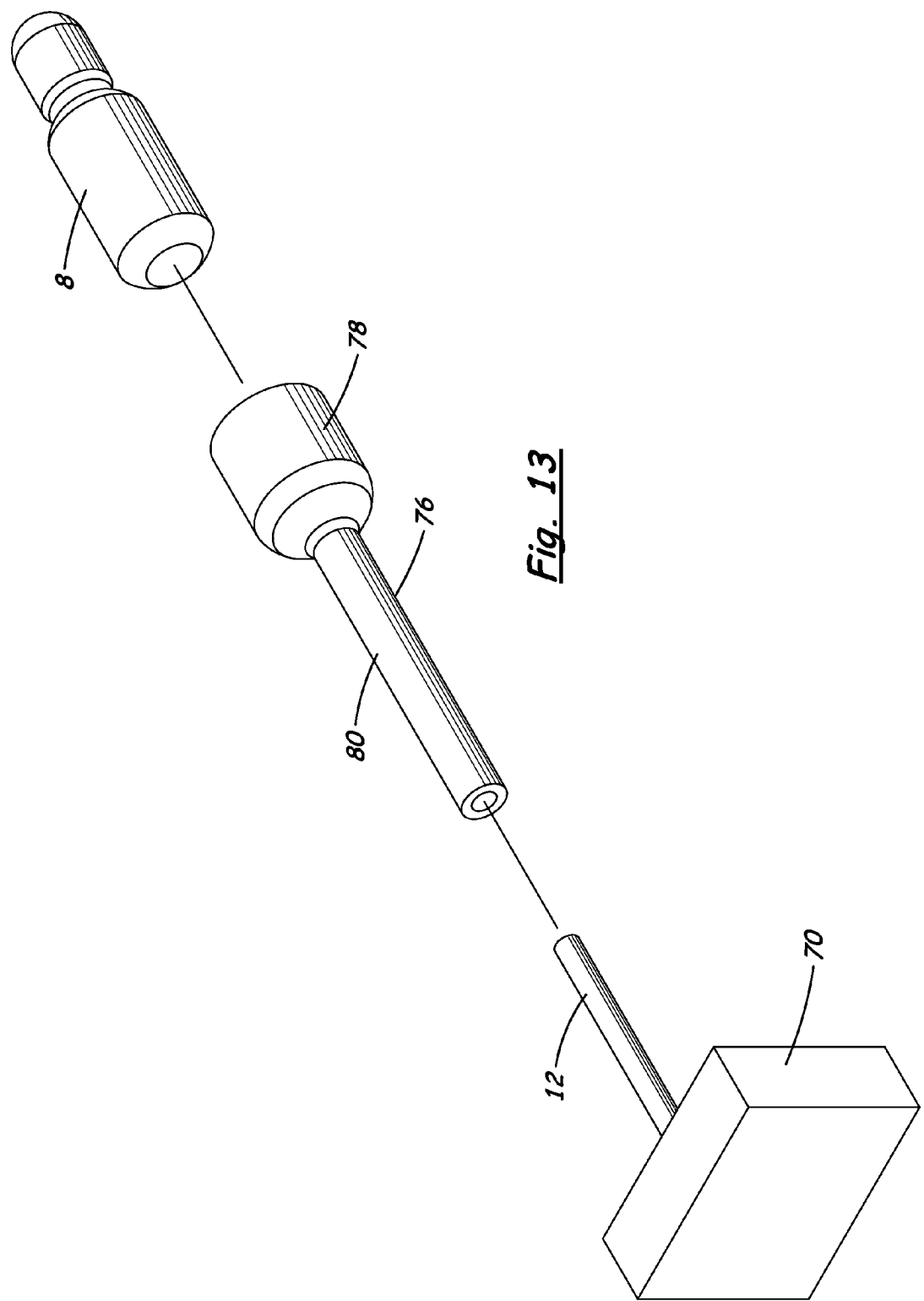
FIG. 13 is a schematic exploded side view of an embodiment of the invention in which the tube includes an enlarged portion for receiving a portion of a vial, according to an illustrative embodiment.
Figure 14:
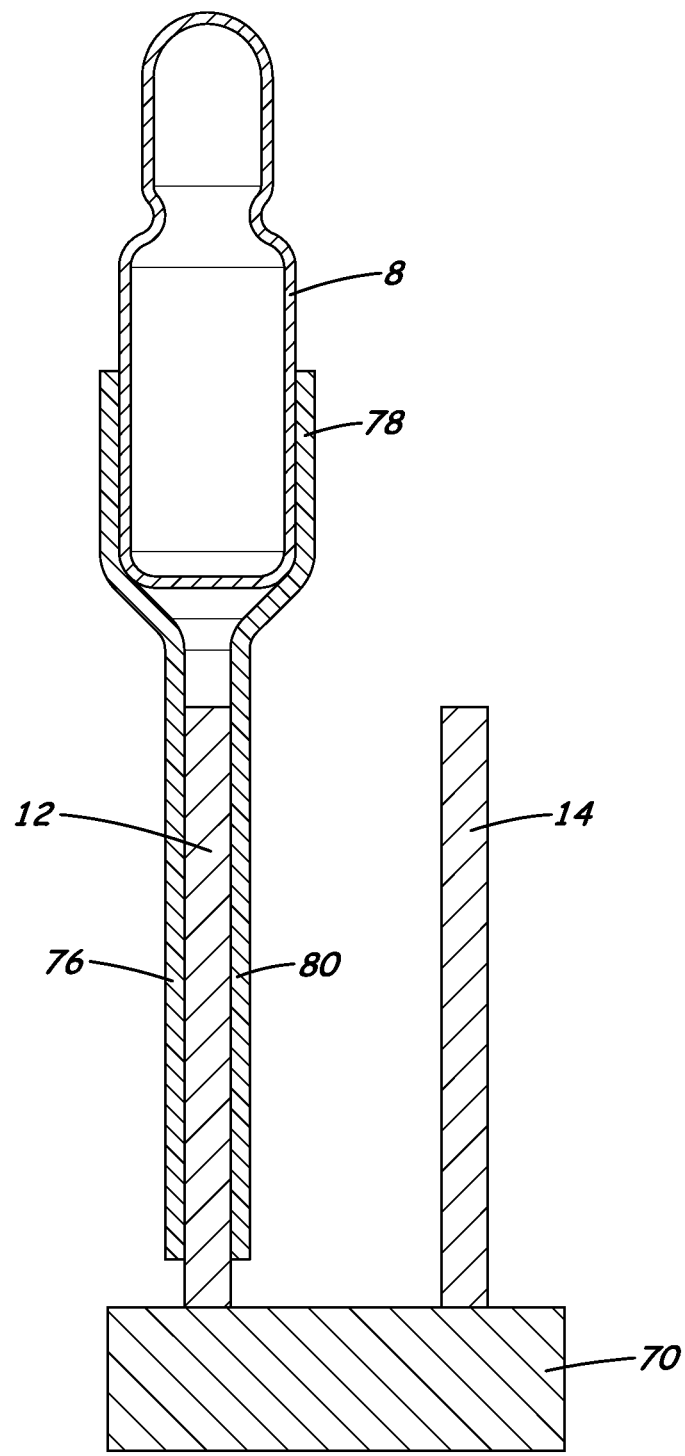
FIG. 14 is a schematic top sectional view of an embodiment of the apparatus in which a tube with an enlarged portion is mounted on one of the elongated elements and a vial is inserted into the enlarged portion.

In other embodiments, such as shown in FIGS. 13 and 14, a tube 74 may be configured to extend beyond the end of the respective elongate element on which it is mounted such that a portion of the tube 76 is not occupied by the element and a hollow cavity is formed adjacent to the end of the elongate element. The cavity may be useful for receiving items, such as the protective cap of a syringe which normally covers the needle of the syringe, but is removed when the syringe is to be used to draw medicine from the vial and perform an injection. The protective cap may be removed from the syringe and the relatively narrow end of the cap may be at least partially inserted into the hollow to be held by the tube until after the medicine has been drawn from the vial and the injection performed, and then the protective cap may be removed from the hollow of the tubing and replaced on the needle of the syringe for disposal.

In some embodiments, a portion 78 of the tube 76 may be enlarged in diameter in comparison to another portion 80 which has a smaller diameter, such as a diameter that is suitable for mounting on one of the elongate elements. The enlarged portion 78 may be suitable for receiving a portion of a smaller vial 8 to hold the vial 8 proximate to the elongate element and the resiliently flexible material of the tube may expend and grip the vial to facilitate accessing the interior of the vial in a suitable manner. The vial is thus held without the use of the hands or fingers of the user while the contents are being withdrawn from the vial. The vial may then be removed from the enlarged portion 78 of the tube 76 when access to the contents of the vial is no longer required.

It should be appreciated from the foregoing description that, except when mutually exclusive, the features of the various embodiments described herein may be combined with features of other embodiments as desired while remaining within the intended scope of the disclosure.

As can be appreciated from the foregoing, bottle holding apparatus system of the invention may have significant benefits to the health care industry, including protecting health care providers and their patients. For example, use of the invention may reduce the likelihood of cross contamination between bottles, which may help in the spread of bacteria such as staph, in health care facilities. As the invention provides a stable mounting of the injectable bottles, unintended discharges of the fluid from the needle are less likely. Also, the chance of the needle breaking during the fluid withdrawal process is diminished. The labels on the bottles may be easier to read, so the possibility of confusing medicine bottles may also be lessened. In high stress areas, such as ambulances and emergency rooms, the invention can hold the bottles in a useful arrangement, and can keep the bottles stable for quick use by the health care professional.

There are also a number of places where the invention may be used, in addition to the obvious hospital and clinic settings. The invention may be employed in ambulances, rescue helicopters, schools, and nursing homes, as well as in the home and even in mobile applications such as the vehicles of persons needing regular injections, such as diabetics. The invention may also be used by fire/rescue and police personnel. The invention may also be highly useful for the administration of non-human injections, such as those injections administered by veterinarians, farmers and ranchers, and zookeepers, as well as scientific personnel in research laboratories.

With respect to the above description then, it is to be realized that the optimum dimensional relationships for the parts of the invention, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A holding system for releasably holding a neck of a bottle holding an injectable fluid, the system comprising:
a base,
mounting structure on the base configured to mount the base on a support;
a pair of elongate elements for releasably gripping the neck of a bottle, the pair of elongate elements having first ends and second ends located opposite of the respective first ends, the elongate elements being spaced from each other to create a gap therebetween, a first one of the elongate elements having a first length between the first and second end of the first element, the first ends of the elongate elements being substantially immovably mounted on the base to maintain a fixed position of the elongate elements with respect to the base, and the second ends being substantially free of connection together; and
a tube having an interior and a length, the interior of a first portion of the length receiving the first elongate element, the interior of a second portion of the interior extending beyond the second end of the first elongate element such that the second portion does not extend into the interior of the second portion to create a hollow cavity in the interior of the tube and permit the second portion to receive and hold an object proximate to the second end of the first elongate element.

2. The system of claim 1 wherein the interior of the tube has a diameter, the first portion having a first diameter and the second portion having a second diameter, the first diameter substantially corresponding to an outer diameter of the first elongate element and the second diameter being larger than the first diameter to create a flared portion of the tube.

3. The system of claim 1 wherein the tube is formed of a resiliently flexible material to expand and grip the object received in the cavity of the second portion of the tube.

4. The system of claim 1 wherein the tube is formed of a resiliently compressible material.

5. The system of claim 1 wherein the base comprises a plate, the first ends of the elongate elements being mounted on the plate at fixed positions on the plate.

6. The system of claim 1 wherein the support comprises a bar and the mounting structure is configured to receive and engage the bar.

7. The system of claim 1 wherein the mounting structure includes an aperture formed in the base, the aperture being configured to receive the support.

8. The system of claim 1 wherein the aperture comprises a hole defined by a continuous edge extending about the hole.

9. The system of claim 8 wherein the mounting structure includes a fastener mounted on the base and configured to releasably engage a portion of the support extending into the aperture, the fastener being movable on the base to releasably abut against the support when a portion of the support is positioned in the aperture.

10. A holding system for releasably holding a neck of a bottle holding an injectable fluid, the system comprising:
a base,
mounting structure on the base configured to mount the base on a support;
a pair of rods for releasably gripping the neck of a bottle, the pair of rods having first ends and second ends located opposite of the respective first ends, the rods being spaced from each other to create a gap therebetween, a first one of the rods having a first length between the first and second end of the first element, the first ends of the rods being substantially immovably mounted on the base to maintain a fixed position of the rods with respect to the base, and the second ends being substantially free of connection together; and
a tube having an interior and a length, the interior of a first portion of the length receiving the first rod, the interior of a second portion of the interior extending beyond the second end of the first rod such that the second portion does not extend into the interior of the second portion to create a hollow cavity in the interior of the tube and permit the second portion to receive and hold an object proximate to the second end of the first rod.

11. The system of claim 10 wherein the interior of the tube has a diameter, the first portion having a first diameter and the second portion having a second diameter, the first diameter substantially corresponding to an outer diameter of the first rod and the second diameter being larger than the first diameter to create a flared portion of the tube.

12. The system of claim 10 wherein the tube is formed of a resiliently flexible material to expand and grip the object received in the cavity of the second portion of the tube.

13. The system of claim 10 wherein the tube is formed of a resiliently compressible material.

14. The system of claim 10 wherein the base comprises a plate, the first ends of the rods being mounted on the plate at fixed positions on the plate.

15. The system of claim 10 wherein the support comprises a bar and the mounting structure is configured to receive and engage the bar.

16. The system of claim 10 wherein the mounting structure includes an aperture formed in the base, the aperture being configured to receive the support.

17. The system of claim 10 wherein the aperture comprises a hole defined by a continuous edge extending about the hole.

18. The system of claim 17 wherein the mounting structure includes a fastener mounted on the base and configured to releasably engage a portion of the support extending into the aperture, the fastener being movable on the base to releasably abut against the support when a portion of the support is positioned in the aperture.

* * * * *